(12) United States Patent
Chen et al.

(10) Patent No.: US 12,381,540 B2
(45) Date of Patent: Aug. 5, 2025

(54) SENSING CIRCUIT AND SENSING METHOD THEREOF

(71) Applicant: Taiwan Semiconductor Manufacturing Company, Ltd., Hsinchu (TW)

(72) Inventors: Tung-Tsun Chen, Hsinchu (TW); Ruey-Bin Sheen, Taichung (TW); Chih-Hsien Chang, New Taipei (TW); Cheng-Hsiang Hsieh, Taipei (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 79 days.

(21) Appl. No.: 18/165,350

(22) Filed: Feb. 7, 2023

(65) Prior Publication Data
US 2024/0171160 A1 May 23, 2024

Related U.S. Application Data

(60) Provisional application No. 63/427,811, filed on Nov. 23, 2022.

(51) Int. Cl.
*H03K 3/354* (2006.01)
*H03K 3/03* (2006.01)

(52) U.S. Cl.
CPC ........... *H03K 3/354* (2013.01); *H03K 3/0315* (2013.01)

(58) Field of Classification Search
CPC .............................. H03K 3/354; H03K 3/0315
See application file for complete search history.

(56) References Cited

U.S. PATENT DOCUMENTS

| | | | | |
|---|---|---|---|---|
| 6,777,991 B2* | 8/2004 | Murakami | ............ | H03L 7/0995 |
| | | | | 327/156 |
| 9,509,289 B2* | 11/2016 | Kobayashi | ............ | H03L 7/0995 |
| 2019/0113476 A1* | 4/2019 | Coln | ............ | G01N 27/3278 |
| 2023/0170798 A1* | 6/2023 | Sareen | ............ | H02M 1/14 |
| | | | | 323/283 |

\* cited by examiner

*Primary Examiner* — Sibin Chen
(74) *Attorney, Agent, or Firm* — JCIPRNET (57) ABSTRACT

A sensing circuit coupled to a sensor includes a first transistor, a second transistor, a third transistor, a fourth transistor, and an oscillator. The first transistor, coupled to a first current source and the sensor, receives a sensing current from the sensor. A gate terminal of the first transistor is connected to a source terminal of the first transistor. The second transistor, coupled to the first transistor and a second current source, generates a first current according to the sensing current. The first current is greater than the sensing current. The third transistor, coupled to the second transistor and the second current source, generates a second current according to the first current. The fourth transistor, coupled to the third transistor, generates a third current. The oscillator is coupled to the fourth transistor. The oscillator generates a signal having an oscillation frequency according to the third current.

20 Claims, 8 Drawing Sheets

SENSING CIRCUIT AND SENSING METHOD THEREOF

CROSS-REFERENCE TO RELATED APPLICATION

This application claims the priority benefit of U.S. provisional application Ser. No. 63/427,811, filed on Nov. 23, 2022. The entirety of the above-mentioned patent application is hereby incorporated by reference herein and made a part of this specification.

BACKGROUND

Over the past decade, bioelectronics have been a vibrant field of research through rapid developments in both fields of electronics and biomedical engineering. Bioelectronics integrates biological materials like proteins, antibodies, DNA, and cells with electronic elements such as field-effect transistors (FETs), electrodes and electrode arrays, and optical resonators to realize functional biosensing devices. Such bioelectronic devices detect and monitor biological interactions and physiological signals by electrical/optical readouts as a means of the change in current, potential, conductance, or resonant frequency. Recently efforts have been made to develop high performance bioelectronic sensing devices and circuits.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. Terms such as "attached," "affixed," "connected" and "interconnected," refer to a relationship wherein structures are secured or attached to one another either directly or indirectly through intervening structures, as well as both movable or rigid attachments or relationships, unless expressly described otherwise.

In addition, terms, such as "first", "second", "third", "fourth" and the like, may be used herein for ease of description to describe similar or different element(s) or feature(s) as illustrated in the figures, and may be used interchangeably depending on the order of the presence or the contexts of the description.

It should be appreciated that the following embodiment(s) of the disclosure provides applicable concepts that can be embodied in a wide variety of specific contexts. The specific embodiment(s) discussed herein is merely illustrative and is related to an integration structure containing more than one type of semiconductor devices, and is not intended to limit the scope of the disclosure. For example, embodiments of the disclosure describe the exemplary manufacturing process of one or more semiconductor devices such as transistors and one or more integration structures such as integrated circuit structures having one or more such semiconductor devices. In the disclosure, the integrated circuit structure may be referred to as a (semiconductor) integrated circuit or a (semiconductor) integrated circuit structure. Certain embodiments of the disclosure are related to an integration structure including semiconductor transistors and other semiconductor devices. Substrates and/or wafers adopted in the exemplary manufacturing process may include one or more types of integrated circuitries or electronic components therein. The semiconductor device(s) may be formed over a bulk semiconductor substrate or a silicon/germanium-on-insulator substrate. In embodiments, the manufacturing method is part of a wafer level packaging process. The embodiments are intended to provide further explanations but are not used to limit the scope of the disclosure. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

A semiconductor device, an integrated circuit (IC) having the same and methods of manufacturing thereof are provided in accordance with various exemplary embodiments. Before addressing the illustrated embodiments specifically, certain advantageous features and aspects of the disclosed embodiments will be addressed generally. The semiconductor device may be adopted in a form of planar-like field effect transistor (planar-like FET) at a back-end-of-line (BEOL) structure of the IC for high device density. Described below is a semiconductor device of a back-gated planar-like FET with a low-dimensional material serving as a channel layer, where the low-dimensional material is capable of providing ideal geometry for an excellent electrostatic control in the operation of the FET while suppressing interface scattering at the interface with an adjacent layer and efficiently dissipating heat during the operation. With such low-dimensional material, the semiconductor device of back-gated planar-like FET can be formed in the BEOL structure of the IC to obtain efficiently heat dissipation and high device performance (with an extremely small foot print area of the IC, for example).

The present efforts have been made to develop high performance bioelectronic sensing devices and circuits by utilizing advanced materials, in particular, low dimensional materials. The low-dimensional material is a two-dimension (2D) material, in the disclosure. The intermediate stages of forming the semiconductor device and/or IC are illustrated in accordance with some embodiments. Some variations of some embodiments are discussed. Throughout the various views and illustrative embodiments, like reference numbers are used to designate like elements.

Thin nanopore membranes in atomic scale are considered to be a promising approach to achieve single base resolution. The ultimate goal is to achieve rapid and cheap DNA sequencing. Recently, the nanopore device for its integration with 2D materials has gained great advances. Various types of DNA exhibit different signal amplitude that has small SNR. Owing to single nucleotide identification and DNA sequencing using biological pores have already been demonstrated their fragility, difficulties related to measuring pA-range ionic currents together with their dependence on biochemical reagents, the solid state nanopore scheme is going to be a promising alternative.

In some embodiments, a sensing circuit that addresses identification of single nucleotides but as well goes beyond DNA sequencing. The use of novel solid state nanopore scheme is based on atomically thin nanopore membranes in 2D materials such as graphene or molybdenum disulfide ($MoS_2$) for DNA strand detection and sequencing.

In some embodiments, the CMOS sensing circuit is capable of amplifying and digitizing very weak electrical current signals. The size of these signals is commensurate with those processed by a new generation of DNA sequencing machines. This application provides a formulated readout circuits and emphasizes not only sensitivity to small signal levels, but also bandwidth and the need to simultaneously operate over parallel channels to properly deal with the constraints as expected to evolve.

In more depth, the purpose of sensing circuits is to simultaneously carry out amplification, filtering, and digitization for individual signals (such as DNA strand signals) as low as 10 picoampere (pA). As a necessity, this design aimed to achieve suitable signal processing quality. The sensing circuit targets the ability to process at sufficient sensitivities (e.g., the current noise is about 1 pA) and speeds (at least 6 kHz) per channel.

Figure 1A:
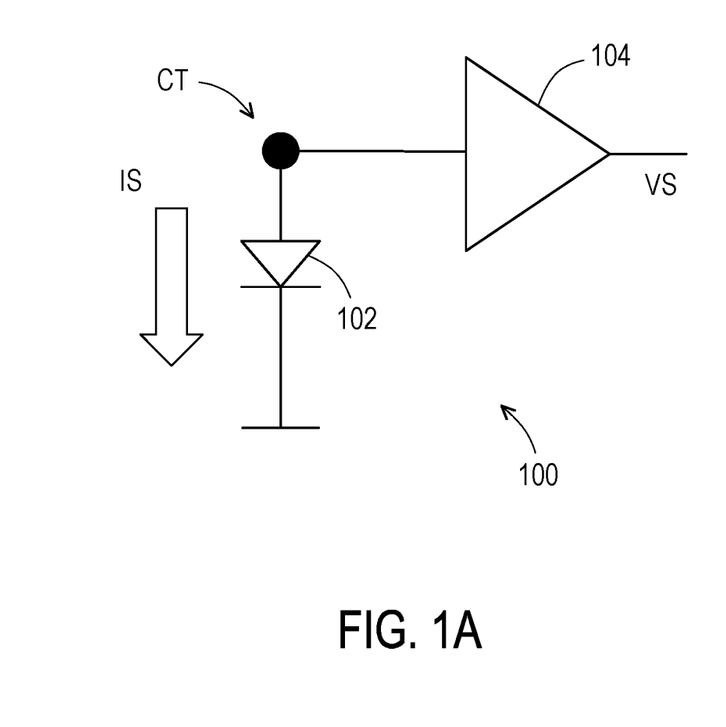
FIG. 1A shows an exemplary scheme of transimpedance amplifier (TIA) architecture with a two-dimension (2D) material nanopore sensor.

FIG. 1A shows an exemplary scheme of transimpedance amplifier (TIA) architecture with a low-dimensional material nanopore sensor.

Referring to FIG. 1A, the TIA 100 at least includes a sensor 102 and an operational amplifier (op-amp or OPA) 104. The sensor 102 is electrically connected to the op-amp through a connection terminal CT. The sensor 102 generates a sensing current IS upon sensing a voltage drop on the sensor 102. The op-amp 104 receives the sensing current IS and transforms the sensing current IS into a sensing voltage VS.

However, it is not easy to achieve high speed and high-resolution detection with general TIA. For biomolecules, for example, the length of DNA base pairs (A/T and C/G) is very short and the time required to pass through the sensor is also very short, so the sensing time required for the sensor is also very short. Therefore, for biomolecules that generate a low current signal through the sensor (e.g., diode, photo diode, or image sensor), the bandwidth of a typical TIA is not high enough (usually below 10 MHz) to provide fast response to accurately detect the electrical signal of the biomolecule.

Figure 1B:
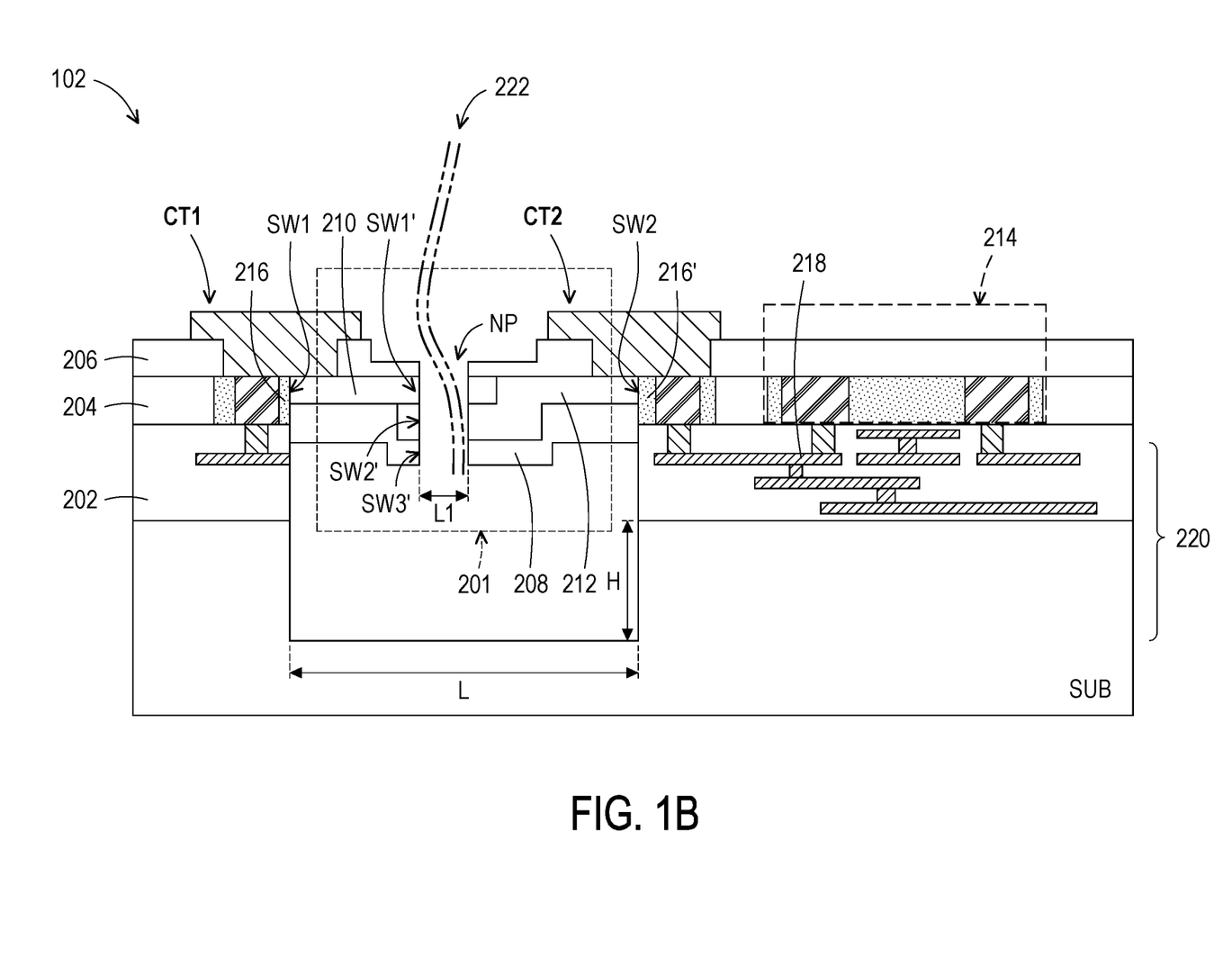
FIG. 1B illustrates a cross-sectional view of some embodiments of a nanopore sensor.

FIG. 1B illustrates a cross-sectional view of some embodiments of a nanopore sensor.

Referring to FIG. 1A and FIG. 1B, the sensor 102 includes a first semiconductor device 201. The first semiconductor device 201 includes a first dielectric layer 206, a gate layer 208, a channel layer 210, a second dielectric layer 212, and source/drain contact terminals CT1, CT2.

In some embodiments, the gate layer 208 is disposed over a substrate SUB. The channel layer 210 is disposed over the gate layer 208. The first dielectric layer 206 is disposed over the gate layer 208 and the channel layer 210. The source/drain terminal CT1 is in contact with the channel layer 210. The channel layer 210 is at least partially sandwiched between the source/drain terminal CT1 and the gate layer 208. The gate layer 208 is disposed between the substrate SUB and the source/drain terminals CT1, CT2.

In some embodiments, the source/drain terminals CT1, CT2 penetrate through the first dielectric layer 206 and partially stand on the first dielectric layer 206. Along a stacking direction of the gate layer 208 and the substrate SUB, the channel layer 210 is next to the source/drain terminal CT1 and overlapped with the portion of the gate layer 208. Part of the channel layer 210 is sandwiched between the second dielectric layer 212 and the first dielectric layer 206, and the source/drain terminal CT1 penetrate through the first dielectric layer 206 to stand on the channel layer 210.

According to one embodiment of the present disclosure, part of the second dielectric layer 212 is sandwiched between the channel layer 210 and the gate layer 208. In some embodiments, the source/drain terminal CT2 penetrate through the first dielectric layer 206 to stand on a portion of the second dielectric layer 212.

According to one embodiment of the present disclosure, the material of the channel layer 210 includes a first low dimensional material. The material of the second dielectric layer 212 includes a second low dimensional material different from the first low dimensional material. The first low dimensional material includes a carbon nanotube, a nanoribbon, a semiconducting two-dimensional material of transition metal dichalcogenides, and combinations thereof.

According to one embodiment of the present disclosure, the semiconductor layer 204 includes the channel layer 210, the second dielectric layer 212, and a portion of the gate layer 208. A sidewall SW1 of the channel layer 210 is in contact with a first spacer 216. A sidewall SW2 of the second dielectric layer 212 is in contact with a second spacer 216'. In some embodiments, the semiconductor layer 204 includes a plurality of second semiconductor devices 214, and the first semiconductor device 201 is electrically coupled to and electrically communicated with at least one of the plurality of second semiconductor devices 214 through the first interconnect structure 218 in the interconnect layer 202. In some embodiments, a sidewall of the first dielectric layer 206 is aligned with a sidewall SW1' of the channel layer 210, a sidewall SW2' of the second dielectric layer 212, and a sidewall SW3' of the gate layer 208.

According to one embodiment of the present disclosure, the length of the gate layer 208 is approximately ranging from 20 μm to 200 μm. In some embodiments, a portion of the first semiconductor device 201 is removed to expose a nanopore NP to detect the current signal of the molecules 222 (e.g., A/T/C/G molecules of the DNA double strands). The aperture (diameter or size) L1 of the nanopore NP is substantially approximately ranging from 1 μm to 2 μm. The portion of the interconnect layer 202 and the portion of the substrate SUB is removed to leave a cavity 220. The portion of the cavity 220 in the substrate SUB has a height H approximately ranging from 5 μm to 50 μm and a length L1 substantially equals to the length of the gate layer 208. In some embodiments, the positioning locations of the opening of the nanopore NP are within the positioning location of the first dielectric layer 206 along the direction Z.

In some embodiments, the substrate SUB may be any type of semiconductor body such as a semiconductor wafer and/or one or more die on a wafer, as well as any other type of semiconductor and/or epitaxial layers, associated therewith. The semiconductor body may include silicon, SiGe, SOI, or the like. The interconnect layer 202 (or inter-level dielectric (ILD) structure) may be a single layered or multiple layered structure, and include silicon oxide ($SiO_2$), silicon oxynitride (SiON), silicon nitride (SiN), silicon carbide (SiC), or the like.

In some embodiments, the first spacer 216 and the second spacer 216' may be an isolation structure. In one embodiment, a material of the first spacer 216 and the second spacer 216' include a dielectric material, such as silicon oxide, silicon nitride, silicon carbide, silicon oxynitride, silicon carbonitride, silicon carbide oxynitride, spin-on glass (SOG), phosphosilicate glass (PSG), borophosphosilicate glass (BPSG), fluorinated silica glass (FSG), carbon doped silicon oxide (e.g., SiCOH), polyimide, and/or a combination thereof. In certain embodiments, the material of the first spacer 216 and the second spacer 216' include a semiconductor material, such as silicon (Si) or germanium (Ge). In alternative embodiments, the material of the first spacer 216 and the second spacer 216' include a metal oxide material, such as sapphire ($Al_2O_3$), indium tin oxide (ITO), or the like. The first spacer 216 and the second spacer 216' may be formed by any suitable forming technique, such as deposition, spin-coating, sputtering, or other suitable methods.

In one embodiment, a material of the source/drain terminals CT1, CT2 may be a connection structure including copper (Cu), copper alloys, aluminum (Al), aluminum alloy, nickel (Ni), manganese (Mn), magnesium (Mg), silver (Ag), gold (Au), tungsten (W), a combination of thereof (e.g., Au/Pt), or the like. The source/drain terminals CT1, CT2 may be formed by deposition and patterning process. The deposition may include electroplating, electroless plating, chemical vapor deposition (CVD, such as plasma enhanced CVD (PE-CVD) and laser-assisted CVD), atomic layer deposition (ALD), and physical vapor deposition (PVD) (such as, sputtering, and e-beam evaporation), a combination thereof, or the like. The patterning process may include photolithography and etching processes. The etching process may include dry etching, wet etching, or a combination thereof.

In some embodiments, a material of the first dielectric layer 206 includes a dielectric material, such as silicon oxide, silicon nitride, silicon carbide, silicon oxynitride, silicon carbonitride, silicon carbide oxynitride, SOG, PSG, BPSG, FSG, carbon doped silicon oxide (e.g., SiCOH), polyimide, a high-k dielectric material, an insulating-like low-dimension material, and/or a combination thereof. It should be noted that the high-k dielectric materials are generally dielectric materials having a dielectric constant greater than 4 or even greater than about 10. High-k dielectric materials include metal oxides. Examples of metal oxides used for high-k dielectric materials include oxides of Li, Be, Mg, Ca, Sr, Sc, Y, Zr, Hf, Al, La, Ce, Pr, Nd, Sm, Eu, Gd, Tb, Dy, Ho, Er, Tm, Yb, Lu, and/or a combination thereof. In some embodiments, the insulating-like low dimension material includes an 2D material having an insulating band-gap property (referred to as "insulating-like 2D material"), such as hexagonal boron nitride (h-BN). In one embodiment, the material of the first spacer 216 is the same as the material of the second spacer 216'. In an alternative embodiment, the material of the first spacer 216 is different from the material of the second spacer 216'.

The first spacer 216 and the second spacer 216' may be formed by CVD (e.g., flowable chemical vapor deposition (FCVD), PE-CVD, high density plasma CVD (HDP-CVD) or sub-atmospheric CVD (SACVD)), molecular layer deposition (MLD), spin-on coating, sputtering, exfoliation (such as mechanical exfoliation and liquid-phase exfoliation) and transfer, gas phase epitaxy, or other suitable methods. In one embodiment, the first spacer 216 and the second spacer 216' may be one-layer structure. In another embodiment, the first spacer 216 and the second spacer 216' may be multi-layer structure. The disclosure is not limited thereto. In some embodiments, the first spacer 216 and the second spacer 216' serves as an insulating layer, which is referred to as an inter-metal dielectric (IMD) layer.

In some embodiments, a material of the channel layer 210 and the second dielectric layer 212 includes carbon nanotube, carbon nanoribbon, a semiconducting-like low-dimension material, and/or a combination thereof. In some embodiments, the semiconducting-like low dimension material includes an 2D material having a semiconducting band-gap property (referred to as "semiconducting-like 2D material"), such as transition metal dichalcogenides or the like. In some embodiments, the transition metal dichalcogenides are represented by a general formula, $NX_2$, where N is a transition metal selected from the groups IVB, VB, or VIB of the periodic table, and X is one element selected from a group consisting of sulfur (S), selenium (Se), and tellurium (Te). For example, the channel layer 210 and/or the second dielectric layer 212 may be a 2D semiconductor layer of $WS_2$, $WSe_2$ or $MoS_2$, however the disclosure is not limited thereto. The material of the channel layer 210 and/or the second dielectric layer 212 has a band-gap size around 1 eV, in some embodiment. In some embodiments, the channel layer 210 may be formed by exfoliation (such as mechanical exfoliation and liquid-phase exfoliation) and transfer, CVD, gas phase epitaxy, or other suitable forming technique.

In some embodiments, the semiconductor layer 204 includes a single-layer structure or a multilayer structure. For example, each layer is a monolayer of nanocrystals. In some embodiments, the formation of the semiconductor layer 204 includes, but not limited to, performing a mechanical exfoliation to obtain a single-layer or few-layer nanocrystals from the native multi-layer structure of a 2D semiconductor material, and then transferring the single-layer or few-layer nanocrystals onto the first dielectric layer 206 via a temporary carrier (not shown). During the transfer, the single-layer or few-layer nanocrystals are placed onto the first dielectric layer 206 by delaminating from the temporary carrier by an electrochemical delamination, and is laminated to the first dielectric layer 206 by a hot roll lamination, for example. If more layers are needed to form the semiconductor layer 204, the above steps can be repeated more than one time, in certain embodiments.

Figure 2:
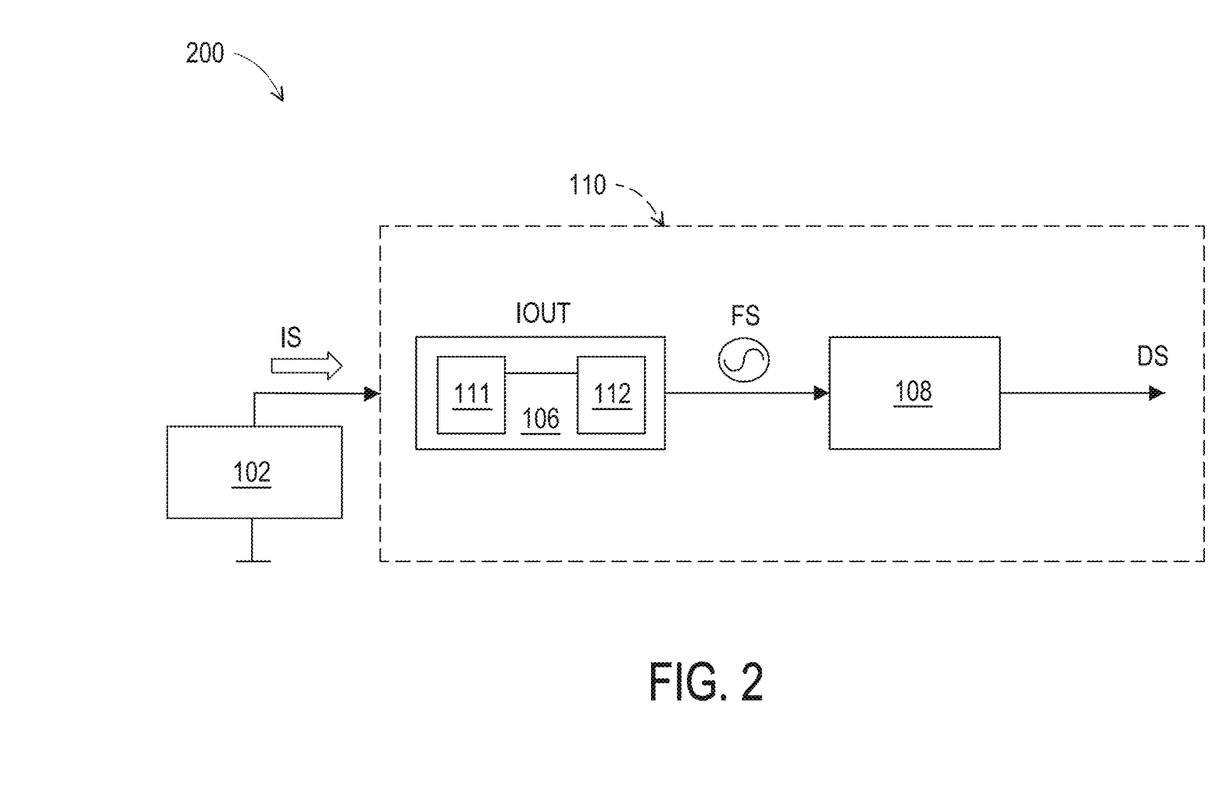
FIG. 2 is a block diagram illustrating a sensing architecture according to one of the embodiments of the disclosure.

FIG. 2 is a block diagram illustrating a sensing architecture according to one of the embodiments of the disclosure.

Referring to FIG. 1B and FIG. 2, in accordance with some embodiments of the disclosure, a circuit 200 includes a sensor 102 and a readout circuit 110. The readout circuit 110 includes a current-controlled oscillator 106 and a frequency counter 108. The current-controlled oscillator (ICO or CCO) 106, electrically connected to the sensor 102, includes a sensing circuit 111 and an oscillator 112. The sensor 102 generates a sensing current IS upon a molecule 222 passing through a nanopore NP. The sensing circuit 111 receives the sensing current IS and generates an output current IOUT in response to the sensing current IS. The oscillator 112 is electrically connected to the sensing circuit 111. The oscillator 112 receives the output current IOUT from sensing circuit 111 and generates a first signal having an oscillation frequency according to or in response to the output current IOUT. For example, the oscillator 112 may output a frequency shift FS based on the variations of the various sensing currents IS inputted to the current-controlled oscillator 106. The frequency counter 108 is electrically connected to the current-controlled oscillator 106. In some embodiments, the frequency counter 108 receives the first signal having the oscillation frequency and a second signal having a reference frequency (as discussed in detail in FIG. 5) and output a digital signal DS. In some embodiments, the first signal with the oscillation frequency is a sinusoidal wave. In some embodiments, the digital signal DS is a periodic continuous square wave. In some embodiments, the output current IOUT is greater than the sensing current IS. In other words, the output current IOUT may be boosted by the sensing circuit 111 in response to the sensing current IS.

Figure 3:
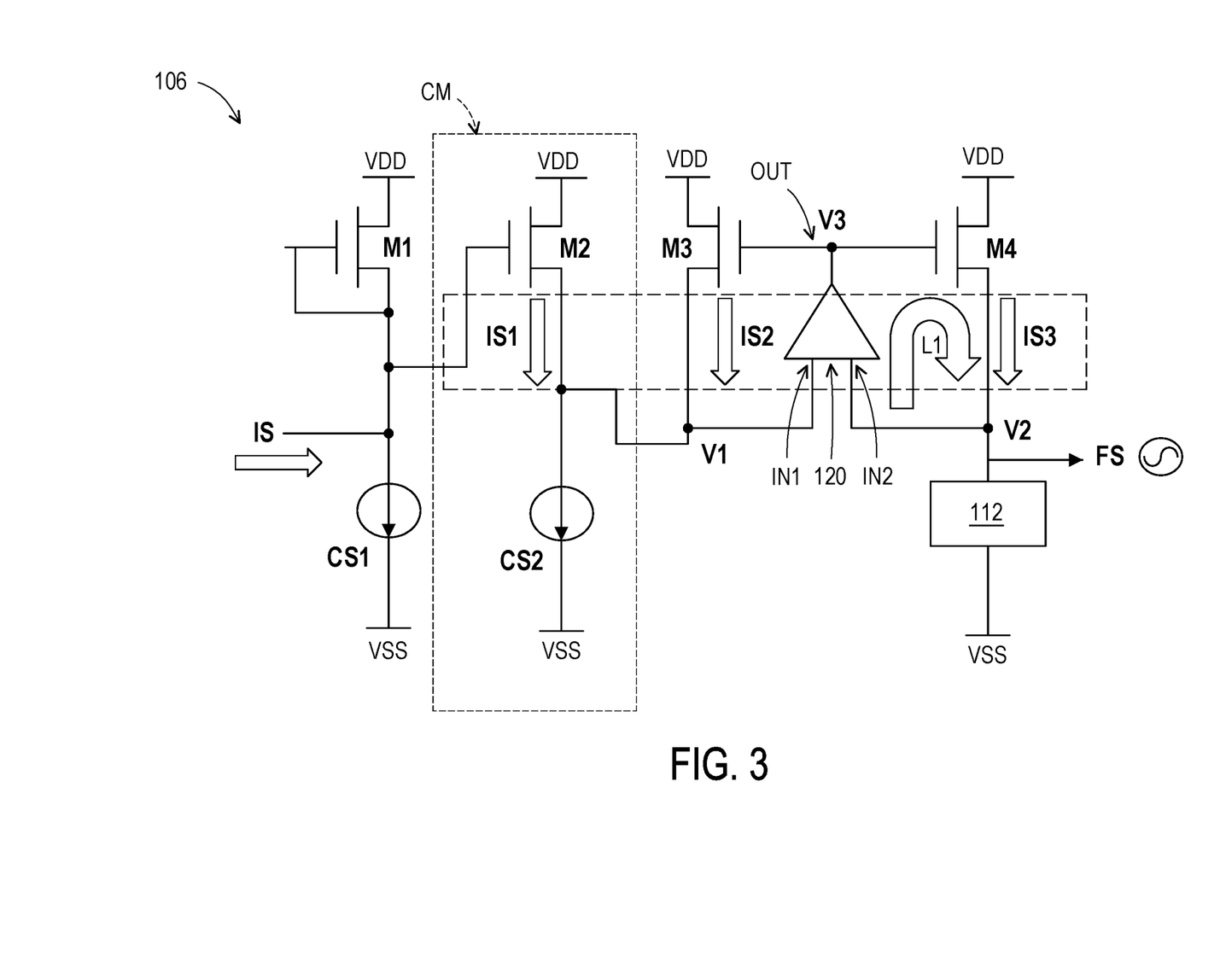
FIG. 3 shows an exemplary scheme of current-controlled oscillator (ICO) according to one of the embodiments of the disclosure.

FIG. 3 shows an exemplary scheme of current-controlled oscillator (ICO) according to one of the embodiments of the disclosure.

Referring to FIG. 2 and FIG. 3, according to one embodiment of the present disclosure, the current-controlled oscillator (ICO) 106 includes a biasing circuit, a current mirror circuit CM, an amplifier 120, and an oscillator 112. The biasing circuit may include a first transistor M1 and a first current source CS1 to provide a stable bias current. The source terminal of the first transistor M1 is electrically connected to a first current source CS1 and the sensor 102. The drain terminal of the first transistor M1 is electrically connected to a power source VDD to provide a bias voltage. The gate terminal of the first transistor M1 is directly connected to a source terminal of the first transistor M1. In other words, the first transistor M1 in the biasing circuit is served as a MOS diode (or active load). The first current source CS1 in the biasing circuit is able to stabilize the variation of the bias voltage (or biasing current from the source terminal of the first transistor M1). The sensing current IS is inputted to the source terminal of the first transistor M1. In some embodiments, the output terminal of the first current source CS1 is electrically connected to the lowest voltage level current-controlled oscillator (ICO) 106 (e.g., the ground voltage VSS).

In accordance with some embodiments of the disclosure, the current mirror circuit CM, connected as a common drain structure, includes a second transistor M2 and a second current source CS2. The drain terminal of the second transistor M2 is electrically connected to a power source VDD. In some embodiments, the output terminal of the second current source CS2 is electrically connected to the lowest voltage level of the current-controlled oscillator (ICO) 106 (e.g., the ground voltage VSS). The gate terminal of the second transistor M2 is electrically connected to the source terminal of the first transistor M1. The source terminal of the second transistor M2 is electrically connected to the second current source CS2. The second transistor M2 generates a first current IS1 according to the sensing current IS. In some embodiments, the first current IS1 is amplified or boosted through the current mirror circuit CM. That is, the first current IS1 is greater than the sensing current IS. As such, the very low sensing current IS generated by biomolecules such as the DNA molecules may be copied and then amplified through the current mirror circuit CM. Therefore, the bandwidth of the current-controlled oscillator 106 may be increased for subsequent detection.

In accordance with some embodiments of the disclosure, the output terminal of the amplifier 120 is electrically connected to a third transistor M3 and a fourth transistor M4. The source terminal of third transistor M3 is electrically connected to the source terminal of the second transistor M2, the second current source CS2, and one input terminal IN1 (for example, a positive input terminal) of the amplifier 120. The drain terminal of the third transistor M3 is electrically connected to a power source VDD. The third transistor M3 generates a second current IS2 according to the first current IS1. In some embodiments, the second current IS2 may be the same as the first current IS1. In some embodiments, the second current IS2 may greater or larger than the first current IS1.

In accordance with some embodiments of the disclosure, the source terminal of fourth transistor M4 is electrically connected to another input terminal IN2 (for example, a negative input terminal) of the amplifier 120 and the input terminal of the oscillator 112. The drain terminal of the fourth transistor M4 is electrically connected to a power source VDD. The fourth transistor M4 generates a third current IS3 according to the first current IS1 or the second current IS2. In some embodiments, the third current IS3 may be the same as the second current IS2. In other words, the first voltage V1 on the positive input terminal IN1 of the amplifier 120 may be substantially the same as the second voltage V2 on the negative input terminal IN2 of the amplifier 120. In some embodiments, the third current IS3 may greater or larger than second current IS2.

In accordance with some embodiments of the disclosure, the amplifier 120 has an output terminal OUT, a first input terminal IN1 (for example, a positive input terminal), and a second input terminal IN2 (for example, a negative input terminal). The output terminal OUT of the amplifier 120 is electrically connected to a gate terminal of the third transistor M3 and a gate terminal of the fourth transistor M4, the second input terminal IN2 is electrically connected to the oscillator 112 and the source terminal of the fourth transistor M4 to form a first loop L1. In some embodiments, the first loop L1 forms negative feedback to compensate an offset between a first voltage V1 of the first input IN1 and a second voltage V2 of the second input IN1. In some embodiments, the amplifier 120 may be one stage op-amp or two-stage op-amp, however, the disclosure is not limited thereto. In some embodiments, the third transistor M3, the fourth transistor M4, and the amplifier 120 may be a proportional-to-absolute-temperature (PTAT) circuit or a bandgap voltage reference circuit. In some embodiments, the PTAT circuit can be used to adjust the voltage difference corresponding to the positive temperature coefficient or the voltage difference corresponding to the negative temperature coefficient. That is, the output terminal OUT of the amplifier 120 connected to the gate terminal of the third transistor M3 and the fourth transistor M4 leads to the almost infinite output impedance, effectively keeping the amplifier 120 at a relatively high gain and reducing the mismatch between the third transistor M3 and the fourth transistor M4. In some embodiments, the output voltage V3 of the amplifier 120 is temperature independent. Therefore, the third current IS3 flows out from the source terminal of the fourth transistor M4 is temperature independent.

In some embodiments, the third current IS3 is M times the sensing current IS, where M is determined by the relative width to length ratio (W/L) of the corresponding transistor. For example, $$M = \frac{(w/L)_3}{(w/L)_1},$$

wherein $(W/L)_1$ and $(W/L)_3$ respectively stands for the relative width to length ratio of the first transistor and the relative width to length ratio of the third transistor. In some embodiments, the width may be adjusted to control the ratio M.

In accordance with some embodiments of the disclosure, one terminal of the oscillator 112 is electrically connected to the source of the fourth transistor M4 while another terminal of the oscillator 112 is electrically connected to the lowest voltage level current-controlled oscillator (ICO) 106 (e.g., the ground voltage VSS).

In accordance with some embodiments of the disclosure, the first transistor M1, the second transistor M2, the third transistor M3, and the fourth transistor M4 may be PMOS. The current mirror CM may be a PMOS type current mirror. Similarly, in accordance with some embodiments of the disclosure, the second transistor M2, the third transistor M3, and the fourth transistor M4 may be NMOS. As such, the current mirror CM may be an NMOS type current mirror (not shown).

In accordance with some other embodiments of the disclosure, the drain terminal of the first transistor M1 is electrically connected to a ground voltage VSS. The gate terminal of the first transistor M1 is directly connected to a drain terminal of the first transistor M1. In other words, the first transistor M1 in the biasing circuit is served as a MOS diode (or active load). The first current source CS1 in the biasing circuit is able to stabilize the variation of the bias voltage (or biasing current from the source terminal of the first transistor MD. The sensing currents IS is inputted to the drain terminal of the first transistor M1. In some embodiments, the input terminal of the first current source CS1 is electrically connected to the power voltage level VDD of the current-controlled oscillator (ICO) 106.

In accordance with some embodiments of the disclosure, the current mirror circuit CM, connected as a common source structure, includes a second transistor M2 and a second current source CS2. The drain terminal of the second transistor M2 is electrically connected to a power source VDD. In some embodiments, the input terminal of the second current source CS2 is electrically connected to the power voltage VDD of the current-controlled oscillator (ICO) 106 while the output terminal of the second current source CS2 is electrically connected to the drain terminal of the second transistor M2. The gate terminal of the second transistor M2 is electrically connected to the drain terminal of the first transistor M1. The drain terminal of the second transistor M2 is electrically connected to the second current source CS2. The second transistor M2 generates a first current IS1 according to the sensing current IS. In some embodiments, the first current IS1 is amplified or boosted through the current mirror circuit CM. That is, the first current IS1 is greater than the sensing current IS.

In accordance with some embodiments of the disclosure, the output terminal of the amplifier 120 is electrically connected to a third transistor M3 and a fourth transistor M4. The drain terminal of third transistor M3 is electrically connected to the drain terminal of the second transistor M2, the second current source CS2, and one input terminal IN1 (for example, a positive input terminal) of the amplifier 120. The source terminal of the third transistor M3 is electrically connected to the lowest voltage level current-controlled oscillator (ICO) 106 (e.g., the ground voltage VSS). The third transistor M3 generates a second current IS2 according to the first current IS1. In some embodiments, the second current IS2 may be the same as the first current IS1. In some embodiments, the second current IS2 may greater or larger than the first current IS1.

In accordance with some embodiments of the disclosure, the drain terminal of fourth transistor M4 is electrically connected to another input terminal IN2 (for example, a negative input terminal) of the amplifier 120 and the output terminal of the oscillator 112. The source terminal of the fourth transistor M4 is electrically connected to the lowest voltage level current-controlled oscillator (ICO) 106 (e.g., the ground voltage VSS). The fourth transistor M4 generates a third current IS3 according to the first current IS1 or the second current IS2. In some embodiments, the third current IS3 may be the same as the second current IS2. In other words, the first voltage V1 on the positive input terminal IN1 of the amplifier 120 may be substantially the same as the second voltage V2 on the negative input terminal IN2 of the amplifier 120. In some embodiments, the first voltage V1 may on the negative input terminal IN1 of the amplifier 120, and the second voltage V2 may on the positive input terminal IN2 of the amplifier 120. In some embodiments, the third current IS3 may greater or larger than second current IS2.

In accordance with some embodiments of the disclosure, the output terminal OUT of the amplifier 120 is electrically connected to a gate terminal of the third transistor M3 and a gate terminal of the fourth transistor M4, the second input terminal IN2 is electrically connected to the oscillator 112 and the drain terminal of the fourth transistor M4 to form a first loop L1. In some embodiments, the first loop L1 forms negative feedback to compensate an offset between a first voltage V1 of the first input IN1 and a second voltage V2 of the second input IN1. In some embodiments, the third current IS3 flowing out from the drain terminal of the fourth transistor M4 is temperature independent.

Figure 4A:
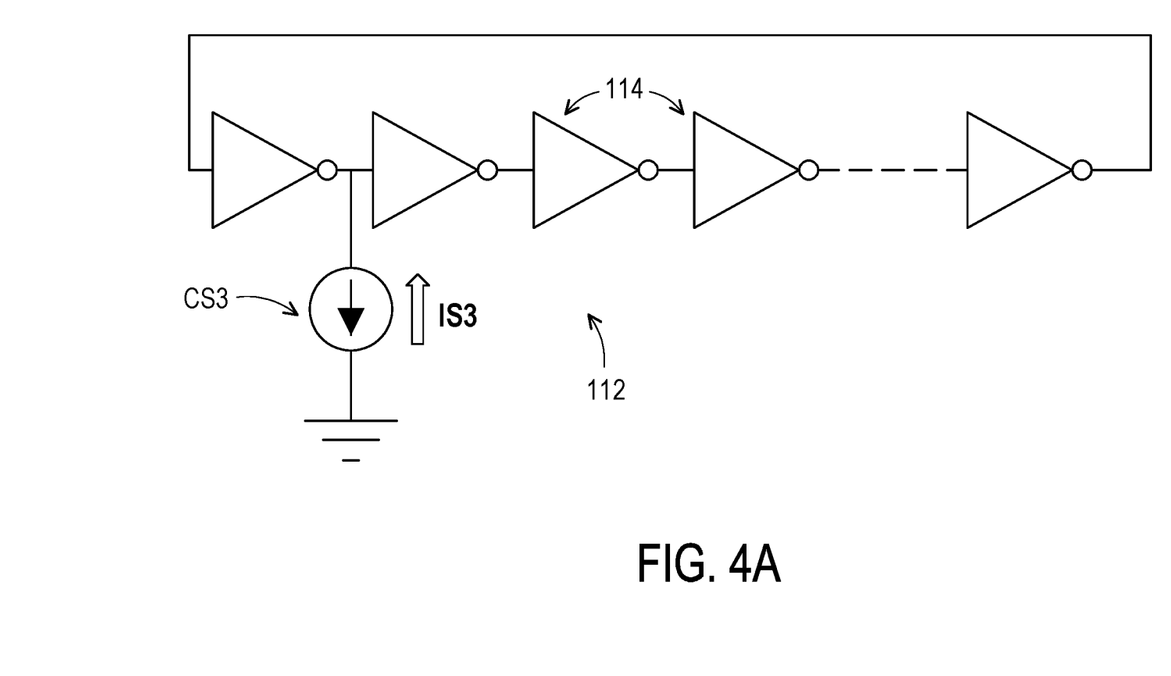
FIG. 4A illustrates an exemplary scheme of ring oscillator according to one of the embodiments of the disclosure.

FIG. 4A illustrates an exemplary scheme of ring oscillator according to one of the embodiments of the disclosure.

Referring to FIG. 3 and FIG. 4A, in accordance with some embodiments of the disclosure, the oscillator 112, includes a plurality of the inverters 114, is an N-stage ring oscillator 112, wherein N is an odd number greater than 3. In other words, the ring oscillator 112 is a circuit composed of an odd number of NOT gates in a ring, whose output oscillates between two voltage levels, representing true ("1") and false ("0"). The NOT gates, or inverters, are attached in a chain and the output of the last inverter is fed back into the first. For example, a simple 3-inverter ring oscillator whose output frequency is 1/(6×inverter delay). According to one embodiment of the present disclosure, the third current IS3 flowing out from the source terminal of the fourth transistor M4 may be treated as an equivalent current source CS3, wherein one terminal of the equivalent current source CS3 is electrically connected to the output terminal of one of the NOT gates.

Figure 4B:
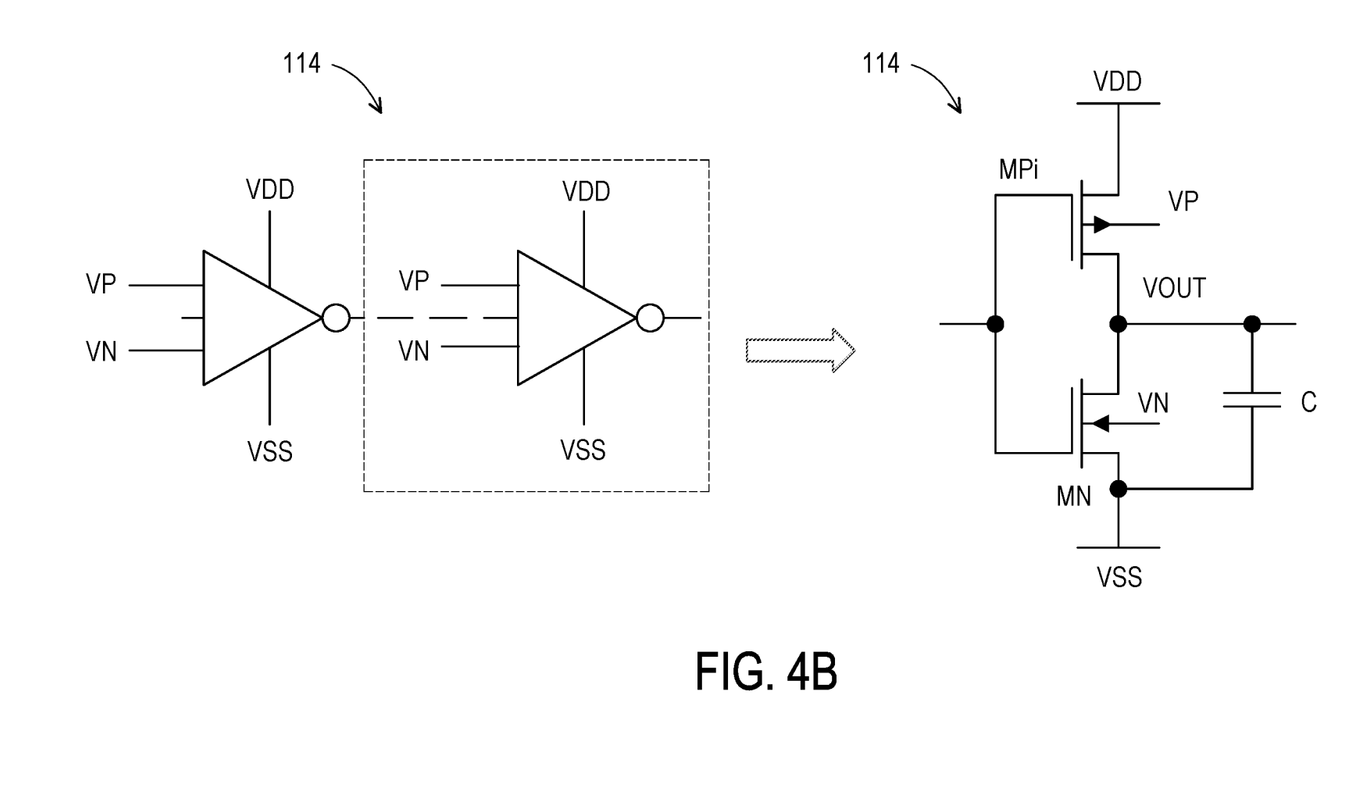
FIG. 4B illustrates an exemplary scheme of an inverter circuit of the ring oscillator according to one of the embodiments of the disclosure.

FIG. 4B illustrates an exemplary scheme of an inverter circuit of the ring oscillator according to one of the embodiments of the disclosure.

Referring to FIG. 4A and FIG. 4B, in accordance with some embodiments of the disclosure, the N-stage ring oscillator 112 in which the single stage is made up of a CMOS inverter where bulk terminals of both transistors ($MP_i$ and $MN_i$, with i=1, 2, ... N and N an odd number greater than 3) are made accessible. An output capacitor C is added at the output of each stage with the aim of setting the oscillation frequency (coarse tuning), and to locally make the single stage insensible to parasitic capacitances. The body potentials VP and VN of both transistors are generated from the auxiliary circuit (not shown). The aim of which is to establish the maximum current flowing in the reference inverter (not shown). In some embodiments, the stages of the ring oscillator 112 are differential stages having two body potentials VP, VN respectively, that are more immune to external disturbances. In some embodiments, this renders available also non-inverting stages. In some embodiments, the ring oscillator 112 may be made with a mix of inverting and non-inverting stages, provided the total number of inverting stages is odd. The oscillator period is in all cases equal to twice the sum of the individual delays of all stages. The ring oscillator only requires power VDD (relative to the ground voltage VSS) to operate. Above a predetermined voltage, typical below the threshold voltage of the MOSFET MP, MN used in the ring oscillator 112, oscillations begin spontaneously. The ring oscillator 112 uses an odd number of inverters 114 to give the effect of a single inverting amplifier with a gain of greater than one. Rather than having a single delay element, each inverter 114 contributes to the delay of the signal around the ring of inverters 114. Adding pairs of inverters 114 to the ring increases the total delay and thereby decreases the oscillation frequency. Changing the supply voltage VDD changes the delay through each inverter 114. For example, applying higher voltages may decrease the delay and increase the oscillation frequency. If T represents the time delay for a single inverter and N represents the number of inverters in the inverter chain, then the frequency of oscillation (f) is given by:

$$f = \frac{1}{2TN}.$$

Figure 5:
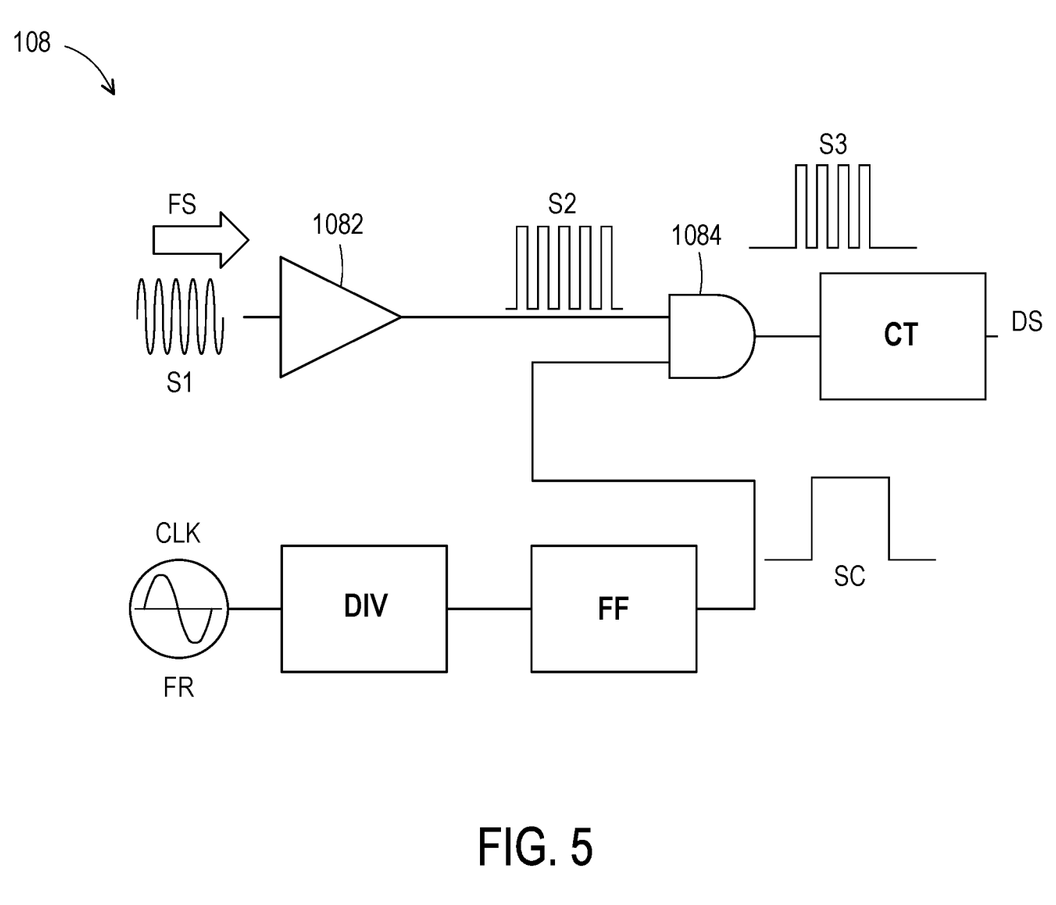
FIG. 5 shows an exemplary scheme of a frequency counter according to one of the embodiments of the disclosure.

FIG. 5 shows an exemplary scheme of a frequency counter according to one of the embodiments of the disclosure.

Referring to FIG. 5, in accordance with some embodiments of the disclosure, the frequency counter 108 includes an input amplifier 1082, a clock CLK, an AND logic gate 1084, a divider DIV, a flip-flop FF, and a counter (or latch) CT. When the first signal S1 having an oscillation frequency FS enters the frequency counter 108, it enters the input amplifier 1082 where the first signal S1 is converted into a second signal S2 with a logic rectangular wave for processing within the circuit in the rest of the counter CT. In some embodiments, the stage of the input amplifier 1082 may contain a Schmitt trigger circuit (not shown) so that noise does not cause spurious edges that would give rise to additional pulses that would be counted. In some embodiments, the input amplifier 1082 is often possible to control the trigger level and also the sensitivity. In some embodiments, the reference frequency FR is controlled according to the input current of the pre-stage circuit or device. For example, the input current may be a third current IS3 from the current-controlled oscillator as has been clarified above.

In accordance with some embodiments of the disclosure, the clock oscillator CLK provides an accurate time-base or clock corresponding to a reference frequency FR to create the various gate or timing signals within the frequency counter 108. In some embodiments, the clock oscillator CLK may be a crystal oscillator. In some embodiments, the clock oscillator CLK may be an oven-controlled crystal oscillator. In some embodiments, there will be the capability to use the external clock oscillator CLK to generate the clock with a predetermined oscillation frequency when it is necessary to lock a number of the oscillation frequency to the same standard.

In accordance with some embodiments of the disclosure, the clock oscillator CLK is used to provide an accurately timed gate enabling signal SC that will allow through pulses from the incoming signal (e.g., the second signal S2). In some embodiments, the clock signal FR generated from the clock oscillator CLK is divided by the divider DIV. In some embodiments, the divider DIV may be a decade divider. The clock signal FR is divided and then is fed into a flip-flop FF to give an enabling pulse for the main gate (e.g., AND logic gate 1084).

In accordance with some embodiments of the disclosure, the AND logic gate 1084 receives the second signal S2 and the accurately timed gate enabling signal SC. The precisely timed gate enabling signal SC from the oscillator CLK is applied to one input of the AND logic gate 1084 and the other has a train of pulses from the incoming signal (e.g., the second signal S2). The resultant output from the AND logic gate 1084 is a series of pulses S3 for a precise amount of time. For example, if the incoming signal was at 1 MHz and the AND logic gate 1084 was opened for 1 second, then 1 million pulses would be allowed through.

In accordance with some embodiments of the disclosure, the counter (or latch) CT receives the incoming pulses S3 from the AND logic gate 1084. In some embodiments, the counter CT has a set of divide-by-10 stages, wherein the number of the stages equals to the number of display digits minus 1. For example, each stage divides by ten and therefore as they are chained, the first stage is that the input divided by ten, the next stage is the input divided by 10×10, and so forth. In some embodiments, the counter CT outputs a digital signal DS without using analog to digital converter (ADC) to drive a display (not shown). In some embodiments, a latch is used in the counter CT to hold the output in place while the figures are being displayed. In some embodiments, the latch will hold the last result while the counter CT is counting a new reading. In this way the display will remain static until a new result can be displayed at which point the latch will be updated and the new reading will be presented to the display. In some embodiments, the display takes the output from the latch and displays the output in a normal readable format. In some embodiments, the display may be liquid-crystal display (LCD), light-emitting diode (LED), or organic light-emitting diode (OLED) displays. In some embodiments, there is a digit for each decade the counter CT can display. In some embodiments, other relevant information may be displayed on the display as well.

Figure 6:
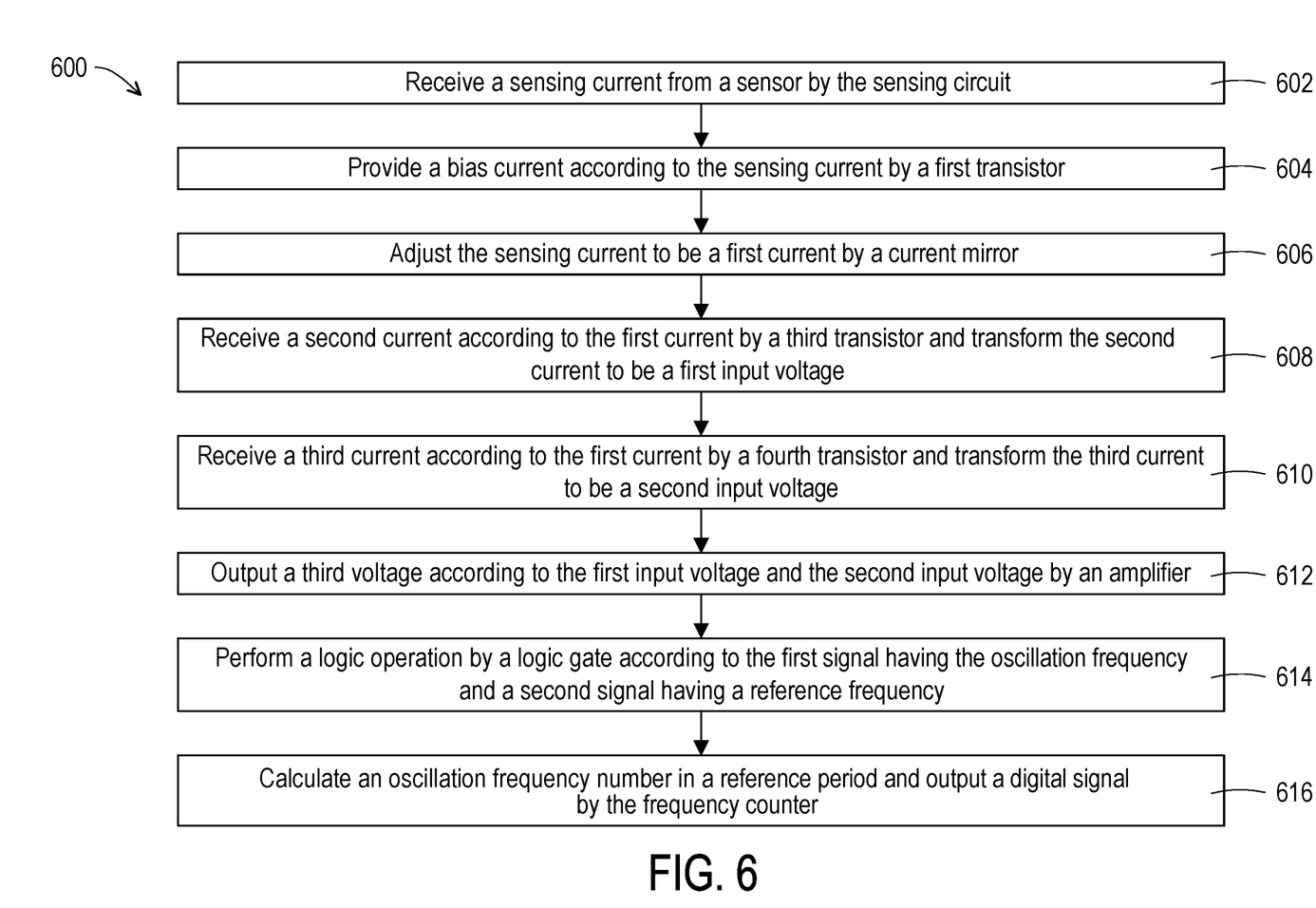
FIG. 6 is a flow diagram illustrating an operation method of the sensing circuit in accordance with one of the embodiments of the disclosure.

FIG. 6 is a flow diagram illustrating an operation method of the sensing circuit in accordance with one of the embodiments of the disclosure.

Referring to FIG. 6, in accordance with some embodiments of the disclosure, the flow diagram 600 of the operation method of the sensing circuit includes the following steps. In step 602, receive a sensing current from a sensor by the sensing circuit. In step 604, provide a bias current according to the sensing current by a first transistor. In step 606, adjust the sensing current to be a first current by a current mirror having a second transistor and a second current source. In step 608, receive a second current according to the first current by a third transistor and transform the second current to be a first input voltage. In step 610, receive a third current according to the first current by a fourth transistor and transforming the third current to be a second input voltage. In step 612, output a third voltage according to the first input voltage and the second input voltage by an amplifier. In step 614, perform a logic operation by a logic gate according to the first signal having the oscillation frequency and a second signal having a reference frequency. In step 616, calculate an oscillation frequency number in a reference period and output a digital signal by the frequency counter.

The present disclosure relates to an integrated circuit having a solid state nanopore sensor. The circuit is applied on high performance application of nanopore biosensing. Therefore, the sensing circuit or readout circuit is able to offer a relatively higher current sensing resolution (about pA level). Further, the circuit is able to provide a relatively higher bandwidth than 10 MHz. As such, the circuit using advanced CMOS technology and low-dimension material drives the possibilities of higher performance biomolecules sensing. In some embodiments, the high sensitivity (frequency/current) of the ICO-based sensing circuit is able to be larger than 5 MHz/nA. In some embodiments, the bandwidth of the ICO-based sensing circuit is able to be larger than 10 MHz (for the settling time is less than 0.1 μs) as the power is approximately ranging from 0.5V to 0.7V and the sensing current is less than 1 nA. In some embodiments, when the current resolution is approximately ranging from 1 pA to 10 pA, the frequency resolution of the clock generator is approximately ranging from 5 KHz to 55 KHz.

According to some embodiments, a sensing circuit coupled to a sensor includes a first transistor, a second transistor, a third transistor, a fourth transistor, and an oscillator. The first transistor, coupled to a first current source and the sensor, receives a sensing current from the sensor. A gate terminal of the first transistor is connected to a source terminal of the first transistor. The second transistor, coupled to the first transistor and a second current source, generates a first current according to the sensing current. The first current is greater than the sensing current. The third transistor, coupled to the second transistor and the second current source, generates a second current according to the first current. The fourth transistor, coupled to the third transistor, generates a third current. The oscillator is coupled to the fourth transistor. The oscillator generates a signal having an oscillation frequency according to the third current.

According to some embodiments, the sensing circuit further includes an amplifier. The amplifier has an output terminal, a first input terminal, and a second input terminal. The output terminal is coupled to a gate terminal of the third transistor and a gate terminal of the fourth transistor, and the second input terminal is coupled to the oscillator and a source terminal of the fourth transistor to form a first loop. In some embodiments, the first loop forms negative feedback to compensate an offset between a first voltage of the first input and a second voltage of the second input. In some embodiments, the sensor includes a first semiconductor device. The first semiconductor device includes a gate layer, a channel layer, a first dielectric layer, and source/drain terminals. The gate layer is disposed over a substrate. The channel layer is disposed over the gate layer. The first dielectric layer is disposed over the gate layer and the channel layer. The source/drain terminals are in contact with the channel layer. The material of the channel layer includes a first low dimensional material. The channel layer is at least partially sandwiched between the source/drain terminals and the gate layer, and the gate layer is disposed between the substrate and the source/drain terminals. In some embodiments, the source/drain terminals penetrate through the first dielectric layer and partially stand on the first dielectric layer, wherein along a stacking direction of the gate layer and the substrate, the channel layer is next to the source/drain terminals and overlapped with the gate layer.

In some embodiments, the first semiconductor device further includes a second dielectric layer. Part of the channel layer is sandwiched between the second dielectric layer and the first dielectric layer, and the source/drain terminals penetrate through the first dielectric layer to stand on the second dielectric layer. In some embodiments, the first semiconductor device further includes a second dielectric layer. Part of the second dielectric layer is sandwiched between the channel layer and the gate layer, and the source/drain terminals penetrate through the first dielectric layer to stand on the second dielectric layer. In some embodiments, a material of the second dielectric layer includes a second low dimensional material different from the first low dimensional material. The first low dimensional material comprises a carbon nanotube, a nanoribbon, a semiconducting two-dimensional material of transition metal dichalcogenides, and combinations thereof. In some embodiments, the sensor further includes a semiconductor layer. The semiconductor layer includes the channel layer, the second dielectric layer, and part of the gate layer. A sidewall of the channel layer is in contact with a first spacer. A sidewall of the second dielectric layer is in contact with a second spacer. In some embodiments, the semiconductor layer includes a plurality of second semiconductor devices, and the first semiconductor device is electrically coupled to and electrically communicated with at least one of the plurality of second semiconductor devices through the first interconnect structure. In some embodiments, a sidewall of the first dielectric layer is aligned with a sidewall of the channel layer, a sidewall of the second dielectric layer, and a sidewall of the gate layer. In some embodiments, the oscillator comprising an N-stage ring oscillator, wherein N is an odd number greater than 3. In some embodiments, the third current is temperature independent.

According to another embodiment, a readout circuit includes a sensor and a current-controlled oscillator. The sensor generates a sensing current upon a molecule passing through a nanopore. The current-controlled oscillator, coupled to the sensor, includes a sensing circuit and an oscillator. The sensing circuit receives the sensing current and generates an output current in response to the sensing current. The oscillator is coupled to the sensing circuit and generates a first signal having an oscillation frequency according to the output current. The output current is greater than the sensing current.

According to some embodiments, the circuit further includes a frequency counter. The frequency counter is coupled to the current-controlled oscillator. The frequency counter receives the first signal having the oscillation frequency and a second signal having a reference frequency and outputs a digital signal. The first signal with the oscillation frequency is a sinusoidal wave. In some embodiments, the sensing circuit includes a first transistor, a second transistor, a third transistor, and a fourth transistor. The first transistor is coupled to a first current source and the sensor. The first transistor receives the sensing current. A gate terminal of the first transistor is connected to a source terminal of the first transistor. The second transistor is coupled to the first transistor and a second current source. The second transistor generates a first current according to the sensing current. The third transistor is coupled to the second transistor and the second current source. The third transistor generates a second current according to the first current. The fourth transistor is coupled to the third transistor. The fourth transistor generates the output current. The first current and the output current are greater than the sensing circuit. In some embodiments, the sensing circuit further includes an amplifier. The amplifier has an output terminal, a first input terminal, and a second input terminal. The output terminal is coupled to a gate terminal of the third transistor and a gate terminal of the fourth transistor. The second input terminal is coupled to the oscillator and a source terminal of the fourth transistor to form a first loop to form negative feedback to compensate an offset between a first voltage of the first input and a second voltage of the second input. In some embodiments, the sensor includes a channel layer with a first low dimensional material and a dielectric layer with a second low dimensional material. The channel layer and the dielectric layer are partially overlapped along a lateral direction.

According yet another embodiment, a method of operating a sensing circuit includes: receiving a sensing current from a sensor by the sensing circuit; providing a bias current according to the sensing current by a first transistor, wherein a gate terminal of the first transistor is connected to a source terminal of the first transistor; adjusting the sensing current to be a first current by a current mirror having a second transistor and a second current source; receiving a second current according to the first current by a third transistor and transforming the second current to be a first input voltage; receiving a third current according to the first current by a fourth transistor and transforming the third current to be a second input voltage; outputting a third voltage according to the first input voltage and the second input voltage by an amplifier; receiving the third current and outputting a first signal having an oscillation frequency by an oscillator; and outputting a digital signal by a frequency counter, wherein the first current is greater than the sensing current. The sensor comprises a channel layer having a first low dimensional material.

In some embodiments, the method further includes: performing a logic operation by a logic gate according to the first signal having the oscillation frequency and a second signal having a reference frequency provided by an external clock; and calculating an oscillation frequency number in a reference period by the frequency counter, wherein the oscillation frequency number is greater than a reference frequency number, wherein the reference period corresponds to the reference frequency, The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A sensing circuit, coupled to a sensor, comprising:
   a first transistor, coupled to a first current source and the sensor, receiving a sensing current from the sensor, wherein a gate terminal of the first transistor is connected to a source terminal of the first transistor, the first current source and the sensor;
   a second transistor, directly coupled to the first transistor and a second current source, generating a first current according to the sensing current, wherein the first current is greater than the sensing current;
   a third transistor, directly coupled to the second transistor and the second current source, generating a second current according to the first current;
   a fourth transistor, coupled to the third transistor, generating a third current; and
   an oscillator, coupled to the fourth transistor; and
   an amplifier, having an output terminal, a first input terminal, and a second input terminal, wherein the output terminal is coupled to a gate terminal of the third transistor and a gate terminal of the fourth transistor, and the second input terminal is coupled to the oscillator and a source terminal of the fourth transistor to form a first loop,
   wherein the oscillator generates a signal having an oscillation frequency according to the third current.

2. The circuit of claim 1, wherein the first loop forms negative feedback to compensate an offset between a first voltage of the first input and a second voltage of the second input.

3. The circuit of claim 1, wherein the sensor comprises a first semiconductor device, comprising:
   a gate layer, disposed over a substrate;
   a channel layer, disposed over the gate layer, wherein a material of the channel layer comprises a first low dimensional material;
   a first dielectric layer, disposed over the gate layer and the channel layer; and
   source/drain terminals, in contact with the channel layer, wherein the channel layer is at least partially sandwiched between the source/drain terminals and the gate layer, and the gate layer is disposed between the substrate and the source/drain terminals.

4. The circuit of claim 3, wherein the source/drain terminals penetrate through the first dielectric layer and partially stand on the first dielectric layer, wherein along a stacking direction of the gate layer and the substrate, the channel layer is next to the source/drain terminals and overlapped with the gate layer.

5. The circuit of claim 3, wherein the first semiconductor device further comprises:

a second dielectric layer, wherein part of the channel layer is sandwiched between the second dielectric layer and the first dielectric layer, and the source/drain terminals penetrate through the first dielectric layer to stand on the second dielectric layer.

6. The circuit of claim 3, wherein the first semiconductor device further comprises:
a second dielectric layer, wherein part of the second dielectric layer is sandwiched between the channel layer and the gate layer, and the source/drain terminals penetrate through the first dielectric layer to stand on the second dielectric layer.

7. The circuit of claim 6, wherein a material of the second dielectric layer comprises a second low dimensional material different from the first low dimensional material, and wherein:
the first low dimensional material comprises a carbon nanotube, a nanoribbon, a semiconducting two-dimensional material of transition metal dichalcogenides, and combinations thereof.

8. The circuit of claim 6, wherein the sensor further comprises:
a semiconductor layer, comprising the channel layer, the second dielectric layer, and part of the gate layer, wherein a sidewall of the channel layer is in contact with a first spacer, wherein a sidewall of the second dielectric layer is in contact with a second spacer.

9. The circuit of claim 8, wherein the semiconductor layer comprises a plurality of second semiconductor devices, and the first semiconductor device is electrically coupled to and electrically communicated with at least one of the plurality of second semiconductor devices through the first interconnect structure.

10. The circuit of claim 6, wherein a sidewall of the first dielectric layer is aligned with a sidewall of the channel layer, a sidewall of the second dielectric layer, and a sidewall of the gate layer.

11. The circuit of claim 1, wherein the oscillator comprises an N-stage ring oscillator, wherein N is an odd number greater than 3.

12. The circuit of claim 1, wherein the third current is temperature independent.

13. A method of operating a sensing circuit, comprising:
receiving a sensing current from a sensor by the sensing circuit;
providing a bias current according to the sensing current by a first transistor, wherein a gate terminal of the first transistor is connected to a source terminal of the first transistor, a first current source and the sensor;
adjusting the sensing current to be a first current by a current mirror having a second transistor directly coupled to the first transistor and a second current source;
receiving a second current according to the first current by a third transistor directly coupled to the second transistor and the second current source and transforming the second current to be a first input voltage;
receiving a third current according to the first current by a fourth transistor and transforming the third current to be a second input voltage;
outputting a third voltage according to the first input voltage and the second input voltage by an amplifier;
receiving the third current and outputting a first signal having an oscillation frequency by an oscillator; and
outputting a digital signal by a frequency counter, wherein the first current is greater than the sensing current,
wherein the sensor comprises a channel layer having a first low dimensional material.

14. The method of claim 13, further comprising:
performing a logic operation by a logic gate according to the first signal having the oscillation frequency and a second signal having a reference frequency provided by an external clock; and
calculating an oscillation frequency number in a reference period by the frequency counter, wherein the oscillation frequency number is greater than a reference frequency number, wherein the reference period corresponds to the reference frequency.

15. A circuit, comprising:
a sensor, generating a sensing current upon a molecule passing through a nanopore; and
a readout circuit, comprising:
a current-controlled oscillator, coupled to the sensor, comprising:
a sensing circuit, receiving the sensing current and generating an output current in response to the sensing current, wherein the sensing circuit comprises:
a first transistor, coupled to a first current source and the sensor, receiving the sensing current from the sensor, wherein a gate terminal of the first transistor is connected to a source terminal of the first transistor, the first current source and the sensor;
a second transistor, directly coupled to the first transistor and a second current source, generating a first current according to the sensing current, wherein the first current is greater than the sensing current;
a third transistor, directly coupled to the second transistor and the second current source, generating a second current according to the first current;
a fourth transistor, coupled to the third transistor, generating the output current; and
an oscillator, coupled to the fourth transistor, generating a first signal having an oscillation frequency according to the output current; and
an amplifier, having an output terminal, a first input terminal, and a second input terminal, wherein the output terminal is coupled to a gate terminal of the third transistor and a gate terminal of the fourth transistor, and the second input terminal is coupled to the oscillator and a source terminal of the fourth transistor to form a first loop,
wherein the output current is greater than the sensing current.

16. The circuit of claim 15, wherein the readout circuit further comprises:
a frequency counter, coupled to the current-controlled oscillator, receiving the first signal having the oscillation frequency and a second signal having a reference frequency and output a digital signal, wherein the first signal with the oscillation frequency is a sinusoidal wave.

17. The circuit of claim 15, wherein the first loop forms negative feedback to compensate an offset between a first voltage of the first input and a second voltage of the second input.

18. The circuit of claim 15, wherein the sensor comprises a channel layer with a first low dimensional material and a dielectric layer with a second low dimensional material, wherein the channel layer and the dielectric layer are partially overlapped along a lateral direction.

19. The circuit of claim 15, wherein the oscillator comprises an N-stage ring oscillator, wherein N is an odd number greater than 3.

20. The circuit of claim 15, wherein the third current is temperature independent.

* * * * *